United States Patent [19]
Kammerer et al.

[11] Patent Number: 5,284,485
[45] Date of Patent: Feb. 8, 1994

[54] ENDOSCOPIC KNOTTING DEVICE

[75] Inventors: Gene W. Kammerer, East Brunswick, N.J.; John N. Semertzides, Cincinnati, Ohio

[73] Assignee: Ethicon, Inc., Somerville, N.J.

[21] Appl. No.: 946,197

[22] Filed: Sep. 16, 1992

[51] Int. Cl.⁵ .............................................. A61B 17/00
[52] U.S. Cl. .................................... 606/148; 606/139; 606/1
[58] Field of Search .................... 606/1, 139, 144, 148, 606/203

[56] References Cited

U.S. PATENT DOCUMENTS

| | | | |
|---|---|---|---|
| 2,012,776 | 8/1935 | Roeder . | |
| 3,476,115 | 11/1969 | Graeff et al. | 606/139 |
| 3,665,926 | 5/1972 | Flores | 606/144 |
| 3,877,434 | 4/1975 | Ferguson et al. | 606/139 |
| 5,037,433 | 8/1991 | Wilk et al. | 606/139 |
| 5,129,912 | 7/1992 | Noda et al. | 606/139 |
| 5,144,961 | 9/1992 | Chen et al. | 128/898 |

FOREIGN PATENT DOCUMENTS 1507354  9/1989  U.S.S.R. ................ 606/144

OTHER PUBLICATIONS

Endoknot, Suture Made with Chromic Gut, Ethicon, Inc. 1991.

Primary Examiner—Stephen C. Pellegrino
Assistant Examiner—Jeffrey A. Schmidt
Attorney, Agent, or Firm—Emil Richard Skula; Matthew S. Goodwin

[57] ABSTRACT

An improved endoscopic device of the type having a surgical needle; a hollow tube; and a filamentary strand attached at its distal end to the surgical needle, and slideably engaged at its proximal end about the tube with a partially tightened slip knot. The improvement in the device relates to means for pulling the filamentary strand through the hollow tube proximally when the surgical needle is detached from the strand. The device can be used to approximate tissue or ligate a vessel.

13 Claims, 7 Drawing Sheets

ENDOSCOPIC KNOTTING DEVICE

BACKGROUND OF THE INVENTION

This invention relates to an endoscopic device, and particularly, to such a device which facilitates the placement and manipulation of a surgical knot endoscopically for tissue approximation and vessel ligation.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs ca be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a tube, conventionally referred to as a cannula, after puncture of a hole into the soft tissue protecting the body cavity. The hole is made with a trocar, which is a sharp-pointed instrument. The trocar includes an obturator, or cutting implement, which is slideably and removably disposed within a trocar cannula. The obturator will puncture a hole in the tissue equal in size to the inner diameter of the trocar cannula. After puncture, the obturator can be slideably withdrawn from the trocar cannula. The surgeon can then perform diagnostic and therapeutic procedures at the surgical site with the aid of specialized instrumentation designed to fit through the trocar cannula and additional trocar cannulas providing openings into the desired body cavity as may be required.

In many surgical procedures, including those involving endoscopic surgery, it is often necessary to tie knots. For example, suturing to approximate tissue requires the formation of a suture knot for placement of a stitch. Additionally, ligating blood vessels to be cut within the surgical site is often necessary in numerous surgical procedures. The vessels may then be severed between the ligations. The primary reason for ligating the vessels is to maintain the surgical site free of an excess of blood and to reduce blood loss in the patient.

Conventionally, surgeons have closed blood vessels with ligatures, which are long, relatively straight strands of suture material. As is the case with the formation of a suture knot to place a stitch, the surgeon must manually tie a knot on the ligature after the ligature is looped around the vessel desired to be closed. Unfortunately, the formation of a knot on sutures and conventional ligatures is tedious and time-consuming during endoscopic surgical applications where a surgeon's manual operative techniques within the surgical site are severely restricted.

In more recent years, a ligature has been developed which is better adapted for endoscopic surgery. ENDOKNOT gut ligature is a device formed from a suture material of surgical catgut. The catgut ligature is securely fastened within a cannula at one end and attached to a needle at the other end. This device is described in the 1991 package insert for the product sold by Ethicon, Inc., which insert is entitled "ENDOKNOT Suture Made With Chromic Gut". Although ENDOKNOT gut ligature facilitates ligation of vessels through small incisions in bodily cavities, the surgeon is required to manually tie the ligature knot extracorporeally, i.e. outside the body, to ligate a vessel. This is a time consuming and laborious process, especially for inexperienced surgeons, and represents a significant disadvantage to the use of the ENDOKNOT ligature device during endoscopic surgery.

The need for manually tying the knot extracorporeally for ligation or tissue approximation was eliminated by using the device described in U.S. Pat. No. 5,144,961. This device has a partially tightened knot secured around a cannula, and the knot can be slid down the cannula onto a suture strand to make a loop which can then be subsequently tightened into a secure knot. Unfortunately, in operation the user must thread the suture strand up through the cannula before sliding the partially tightened knot down the cannula to make the loop. This threading operation is undesirable because it is time consuming and tedious. A similar device is shown in U.S. Pat. No. 2,012,776.

In view of the significant deficiency of the prior art, an endoscopic knotting device which avoids manually tying knots extracorporeally, and threading the suture strand through the cannula, would be highly desired within the medical community.

SUMMARY OF THE INVENTION

The invention is an improved endoscopic device. This device is an improvement over the device described in U.S. Pat. No. 5,144,961. The device is of the type having a surgical needle; a hollow tube; and a filamentary strand attached at its distal end to the surgical needle, and slideably engaged at its proximal end about the tube with a partially tightened slip knot. The improvement comprises means for pulling the filamentary strand through the hollow tube proximally when the surgical needle is detached from the strand.

The endoscopic device of this invention is particularly well suited for approximating bodily tissue and ligating vessels endoscopically. The user of the device is not required to manually tie a knot extracorporeally to ligate or approximate bodily tissue, and, significantly, the user does not need to thread the filamentary strand through the hollow tube; i.e. the cannula, to perform the steps necessary to ligate a vessel or approximate bodily tissue.

The device may be used during endoscopic surgery for numerous applications in which the approximation of bodily tissue, or the ligation of a bodily vessel, is desired.

DETAILED DESCRIPTION OF THE PREFERRED EMBODIMENT

As used in this specification, the word "distal" is used to describe that portion of the device which extends away from the user during use, and the word "proximal" is used to describe that portion of the device that extends toward the user during use. Similarly, "distally" refers to movement extending away from the user during use of the device, and "proximally" refers to movement extending toward the user.

Figure 1:
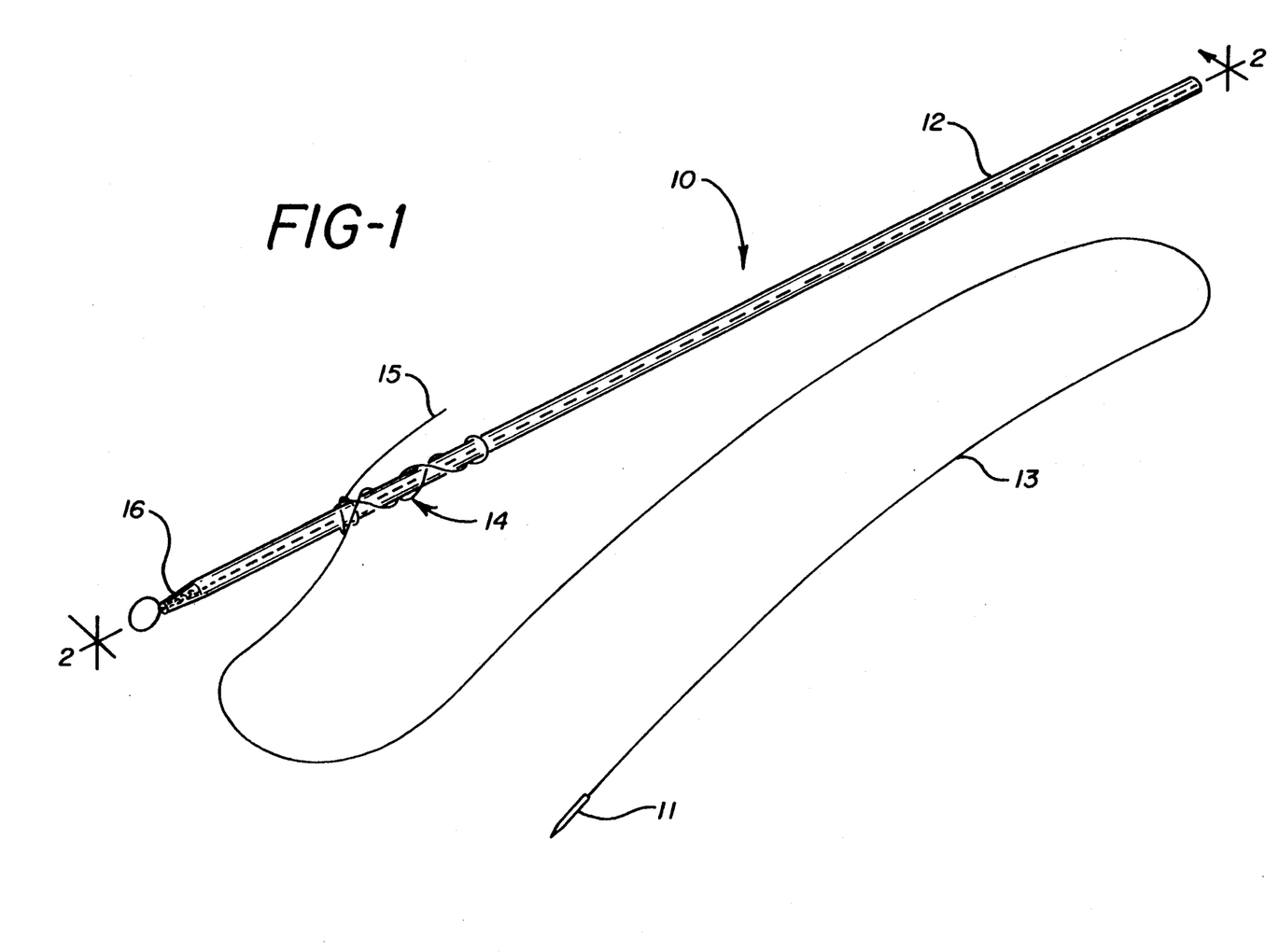
FIG. 1 is a perspective view of the endoscopic device of t is invention.

Referring now to FIG. 1, there is shown an endoscopic device 10 within the scope of the present invention. The device has a surgical needle 11, a hollow tube 12, and a filamentary strand 13. The filamentary strand is attached at its distal end to the surgical needle, and is slideably engaged at its proximal end about the tube with a partially tightened slip knot 14 having a knot pulling end 15. Hollow tube 12 has a tapered distal portion 16, and is shaped as an elongate cylinder with a continuous opening extending axially therethrough. The cross-sectional diameter of the continuous opening at all points along the length of the cylinder is greater than the cross-sectional diameter of the filamentary strand to facilitate the passage of the strand through the tube when the needle is detached, as described in detail below. Preferably, the cross-sectional diameter of the opening is greater than twice the strand cross-sectional diameter. Hollow tube 12 is preferably composed of a flexible plastic, and the opening extending axially therethrough has a substantially constant cross-sectional diameter.

The filamentary strand 13 can be attached to the needle using standard needle attachment. Alternatively, it can be attached using removable or detachable needle attachment. In the case of standard needle attachment, the strand is securely attached to the needle and is not intended to be separated from the needle except by cutting or severing the strand. Removable needle attachment, by contrast, is such that the needle is separable from the strand in response to a force exerted by the surgeon, as illustrated, for example, in European Patent Application 0 420 605 and U.S. Pat. No. 3,926,194.

The filamentary strand can be composed of any surgical suture material. Suture materials can be composed of synthetic and nonsynthetic filaments, as well as absorbable and nonabsorbable fibers. Examples of suitable nonabsorbable suture materials include, but are not limited to, nylon, polypropylene, steel, and polyethyleneteraphthalate (PET). The preferred suture materials are synthetic bioabsorbable suture materials. Examples of suitable bioabsorbable suture materials are those which are derived from the polymerization of lactone monomers, e.g. glycolide, lactide, p-dioxanone and $\epsilon$-caprolactone.

Figure 2:
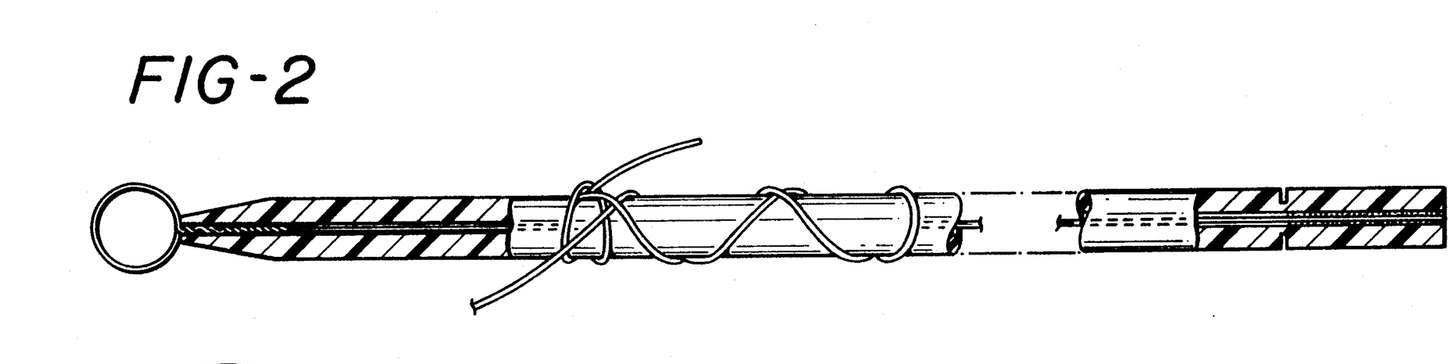
FIG. 2 is a side view in partial cross-section taken along line 2—2 of FIG. 1.
Figures 2A, 3:
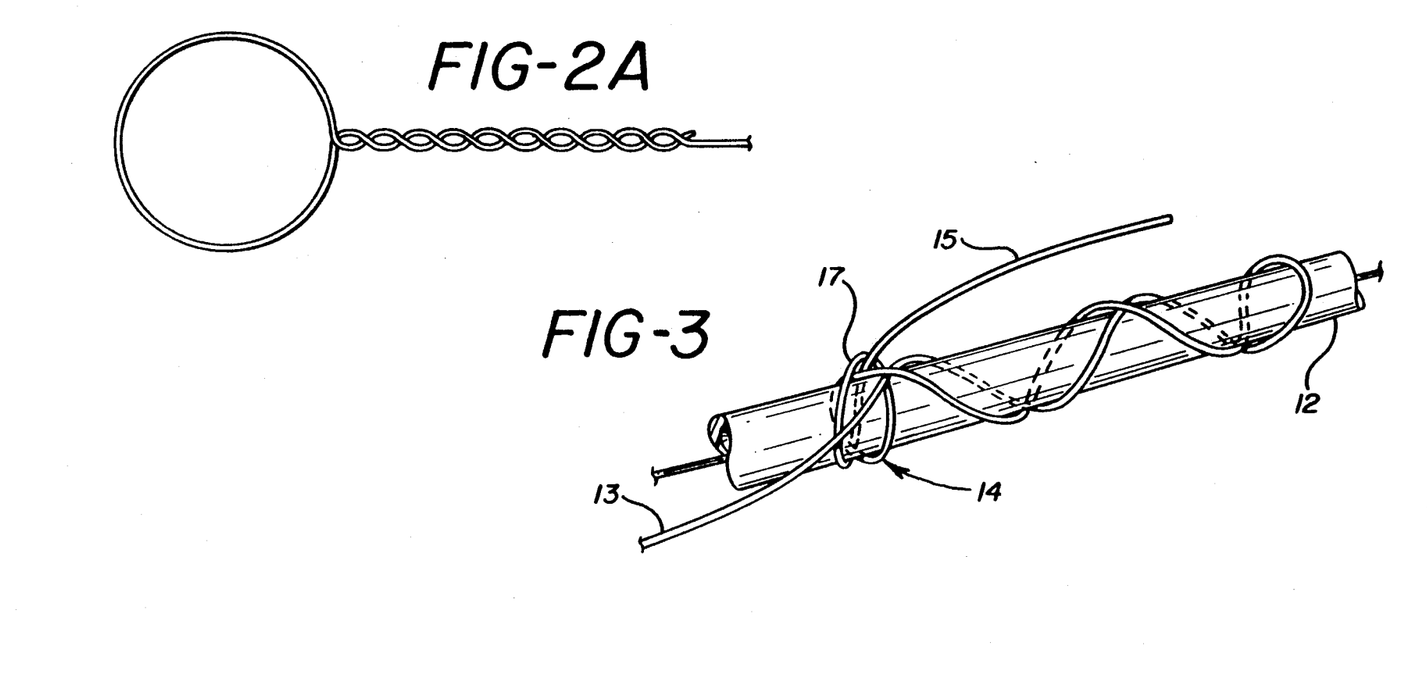
FIG. 2A is an enlarged detail view of a portion of a wire-like member, which forms part of the preferred endoscopic device of this invention.
FIG. 3 is an enlarged fragmentary perspective view of the partially tightened slip knot for the endoscopic device.

Referring now to FIGS. 1, 2 and 2A in combination, the preferred device includes a wire-like member 31 extending through the continuous opening of the hollow tube. The wire-like member can be made of any flexible and deformable material, but it is preferably a stainless steel wire for convenience. The wire is attached by gluing or cementing its proximal end to the proximal end of the hollow tube. At its distal end, it protrudes out from the tapered distal portion 16 of the hollow tube, and is shaped into deformable distal loop 32 as shown in FIG. 2A, which loop abuts the distal end of the tube. The diameter of the loop is greater than the continuous opening in the hollow tube (this opening would represent the inner cross-sectional diameter of the tube). This facilitates inserting a portion of the filamentary strand through the loop, which is a necessary step to eliminate the need to thread the strand through the tube, as described in more detail in conjunction with FIGS. 5A–5H.

The preferred device also includes a frangible proximal end portion 33 on the hollow tube 12. The frangible portion of the hollow tube houses that portion of the wire-like member which is attached to the proximal end of the tube. When the frangible portion of the tube is broken free at score line 34 and pulled away from the remainder of the tube, it pulls the entire wire-like member with it. As the frangible portion is pulled away, the loop of the wire-like member deforms to fit and slide through the continuous opening of the hollow tube.

FIG. 3 illustrates in further detail the knot configuration of the partially tightened slip knot 14. Specifically, filamentary strand 13 is encircled about the proximal end of the tube to form five loosely engaged loops of the partially tightened knot. The remaining length of the filamentary strand is then extended through a loop formation 17 to form the pulling end 15 of the filamentary strand. It should be understood that the number of loops used in forming the knot 14 is not limited to the specific embodiment shown. All that is necessary is that a partially tighten slip knot is configured in such a manner that when fully tightened it allows sliding movement proximally and prevents such sliding movement distally.

Figure 4:
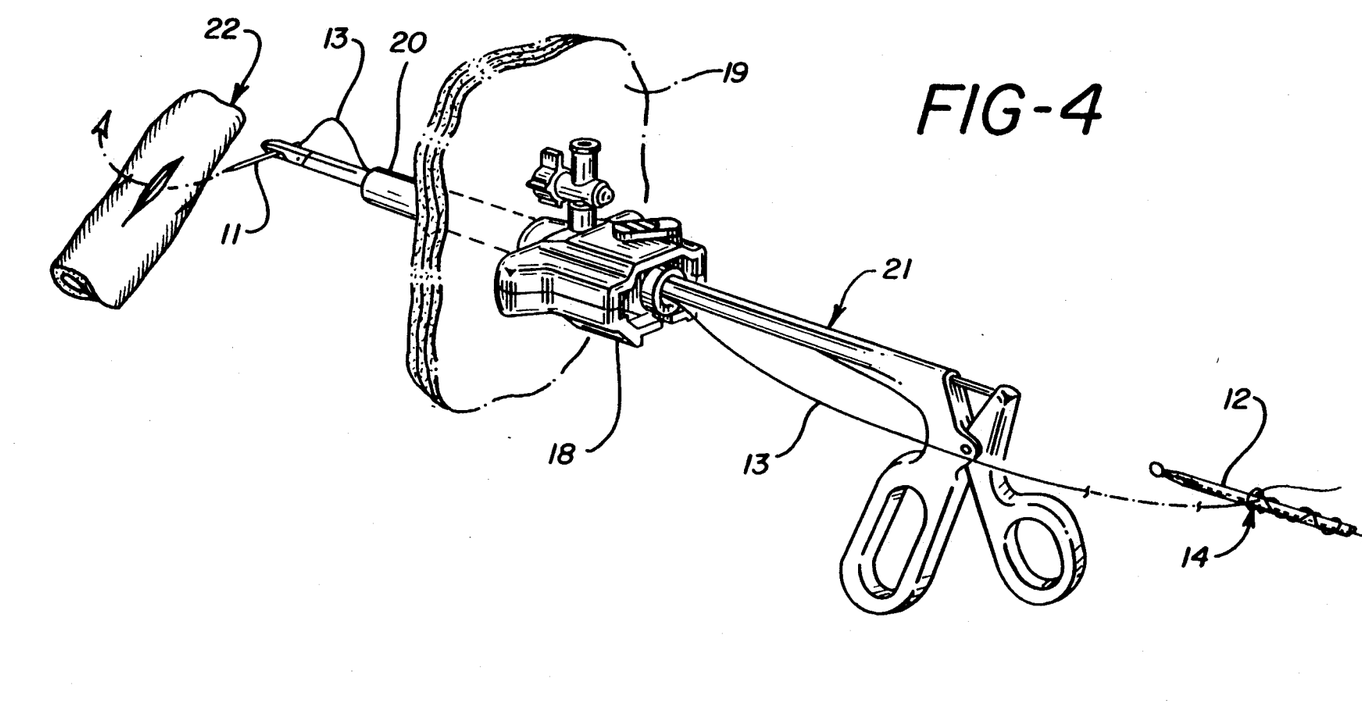
FIG. 4 is a perspective view of conventional surgical instrumentation designed to be used with the endoscopic device.

To approximate tissue using the device, the user would first grasp the distal end of the strand adjacent to the needle with a suitable endoscopic grasping instrument, and then insert this portion of the strand with the needle into and through an appropriately sized trocar. The trocar provides access into a body cavity where the desired tissue approximation is to occur. As illustrated in FIG. 4, the needle and a portion of the filamentary strand penetrate bodily tissue 19 through trocar 18 and trocar cannula 20 to reach the body cavity. A suitable needle grasping instrument 21 is then used to grasp surgical needle The needle is passed through the desired bodily tissue 22 by passing the needle in the direction of the arrow as shown.

Figure 5A:
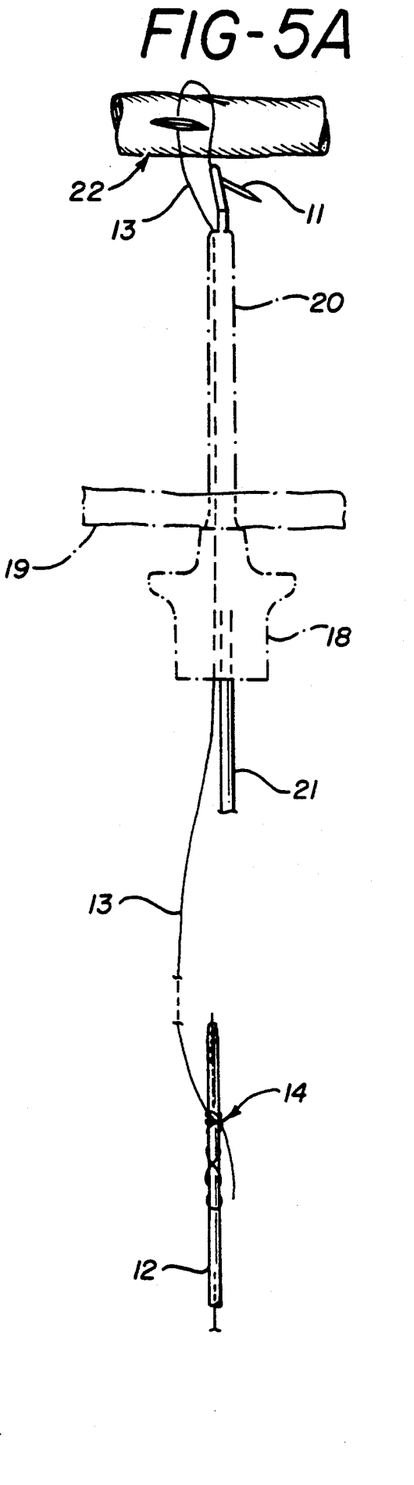
FIGS. 5A through 5H are schematic top plan views illustrating the sequence of steps required to approximate bodily tissue using the endoscopic device.
Figure 5B:
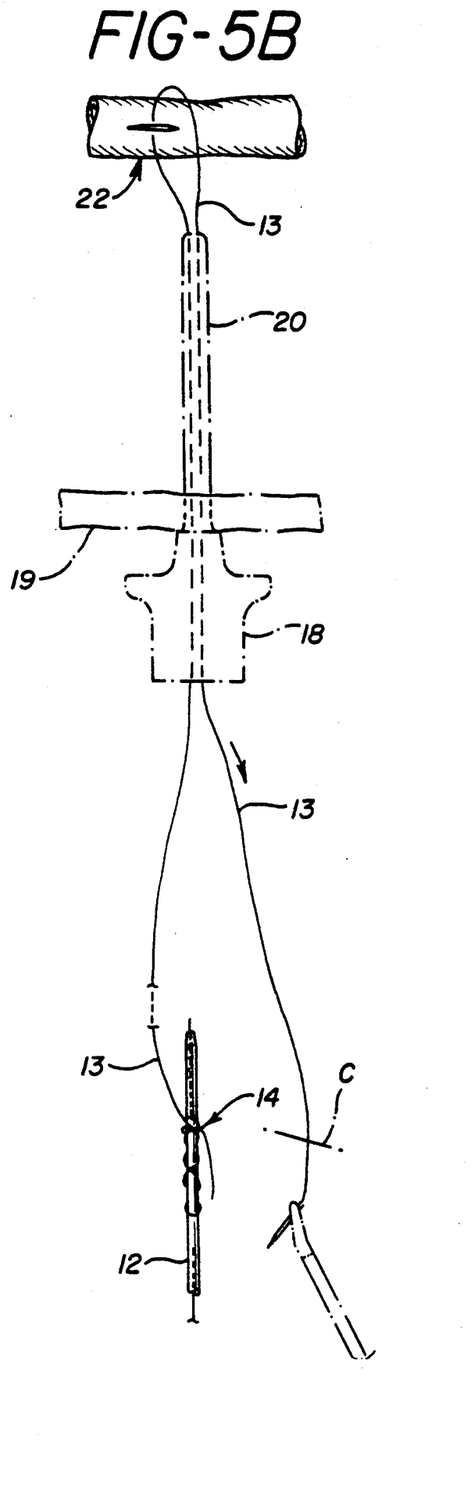
Figure 5C:
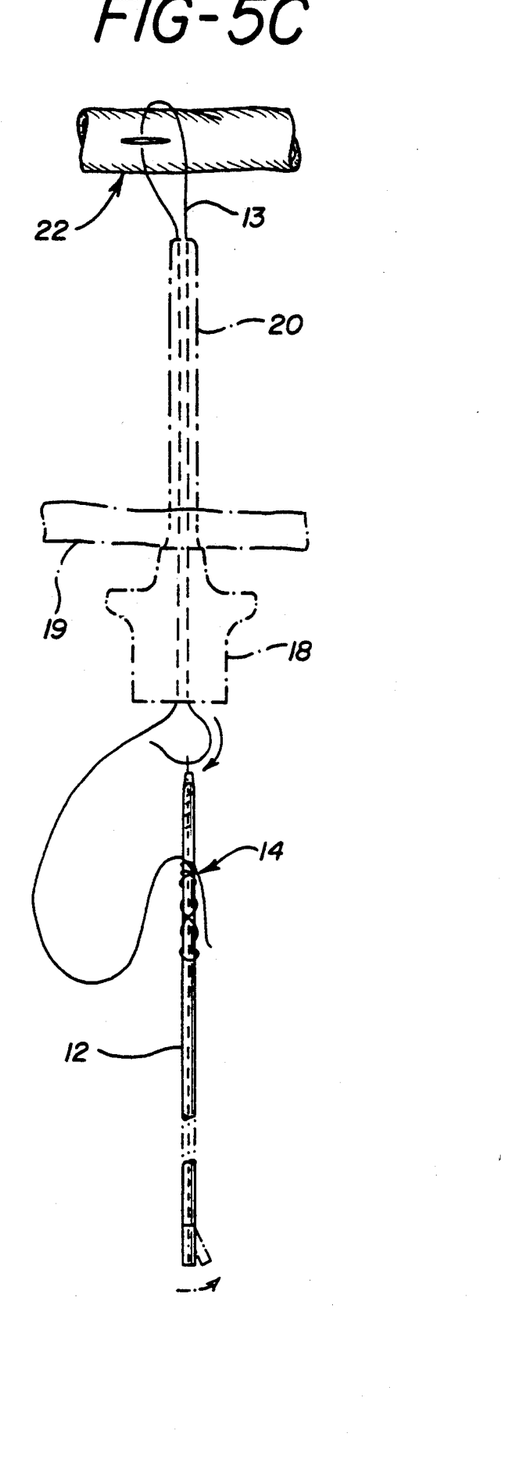

Referring now to FIGS. 5A–5H, once the needle is passed through the tissue to be approximated, it is then pulled proximally in the direction of the arrows of FIGS. 5A and 5B, back up through the trocar until the needle and a portion of the strand exit the trocar outside the body. At this point, the needle is removed from the strand by cutting the strand, for example, near the attachment for the needle as indicated by the designation "C" in FIG. 5B. The remaining tip of the strand is then inserted through the deformable loop of the wire-like member (FIG. 5C).

Figure 5D:
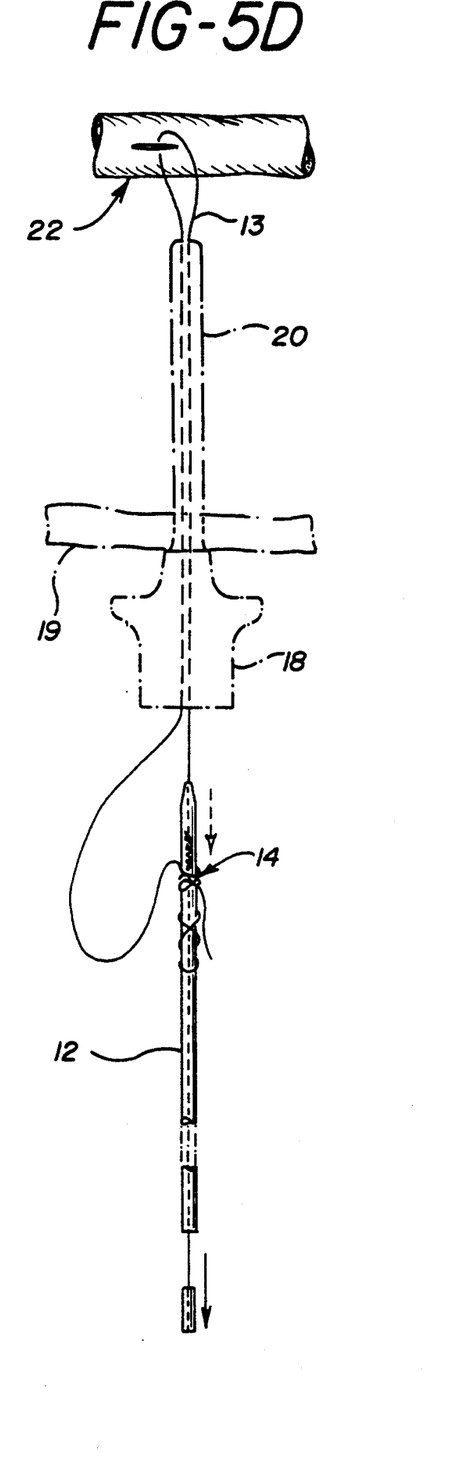
Figure 5E:
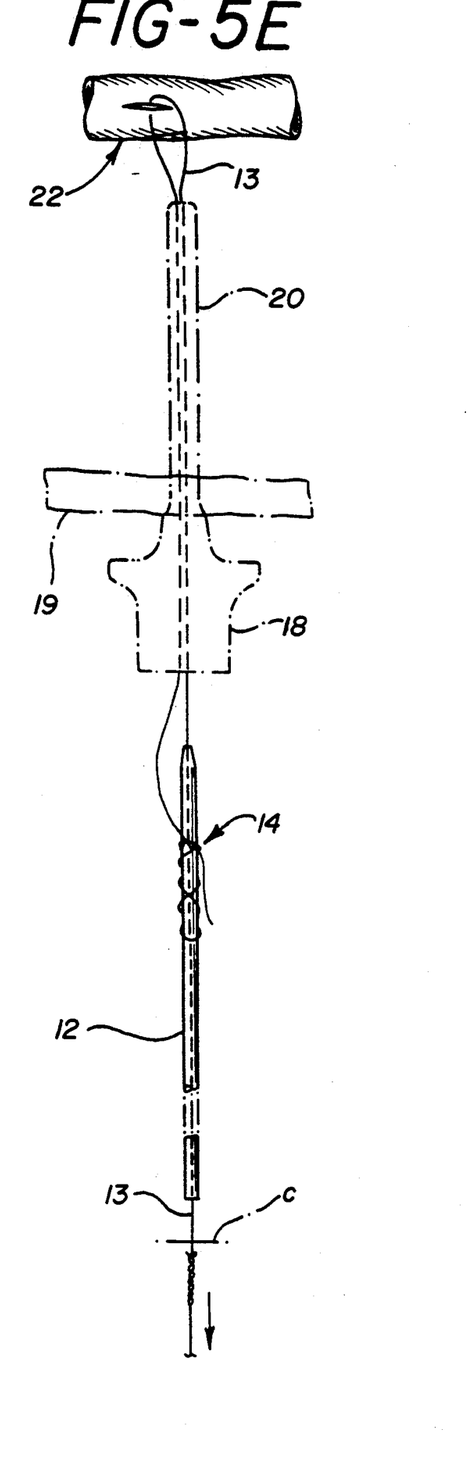

When the loop has received a portion of the strand, a convenient and simple procedure can be carried out to pass the strand proximally through the hollow tube until the strand protrudes from the proximal end of the tube. This procedure does not require manually threading the strand through the tube, and is described as follows. With the strand inserted through the loop, the user would grasp the frangible proximal end portion of the hollow tube, and snap it off at the score line (FIG. 5C). Once the frangible portion is separated from the remainder of the hollow tube, it is pulled proximally (FIG. 5D). Since the wire-like member is attached to the proximal end of the hollow tube within the separated frangible portion, the pulling force on the frangible portion creates a corresponding pulling action on the wire-like member. This force causes the loop on the wire-like member which is abutting the tapered distal end of the hollow tube to deform because its diameter is greater than the inner cross-sectional diameter of the tube. The deformed loop ensnares the strand received through it, and is subsequently pulled proximally with the strand into and through the hollow tube as the separated frangible portion is continually pulled proximally. When the wire-like member and a portion of the strand protrude from the proximal end of the remainder of the hollow tube, the strand can be cut as illustrated in FIG. 5E, and the frangible portion with the wire-like member can be subsequently discarded.

Figure 5F:
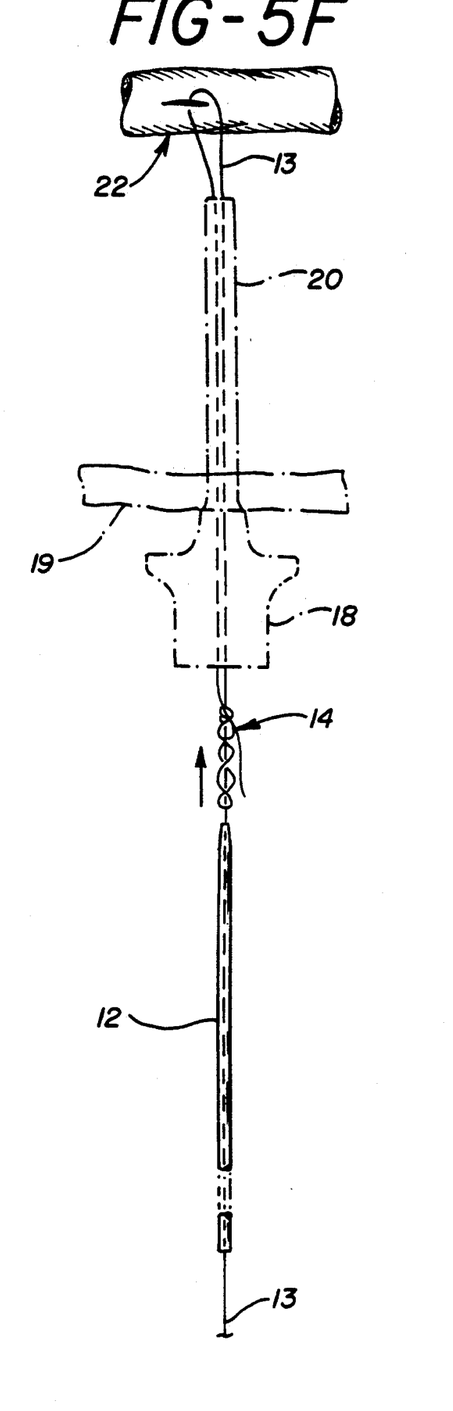
Figure 5G:
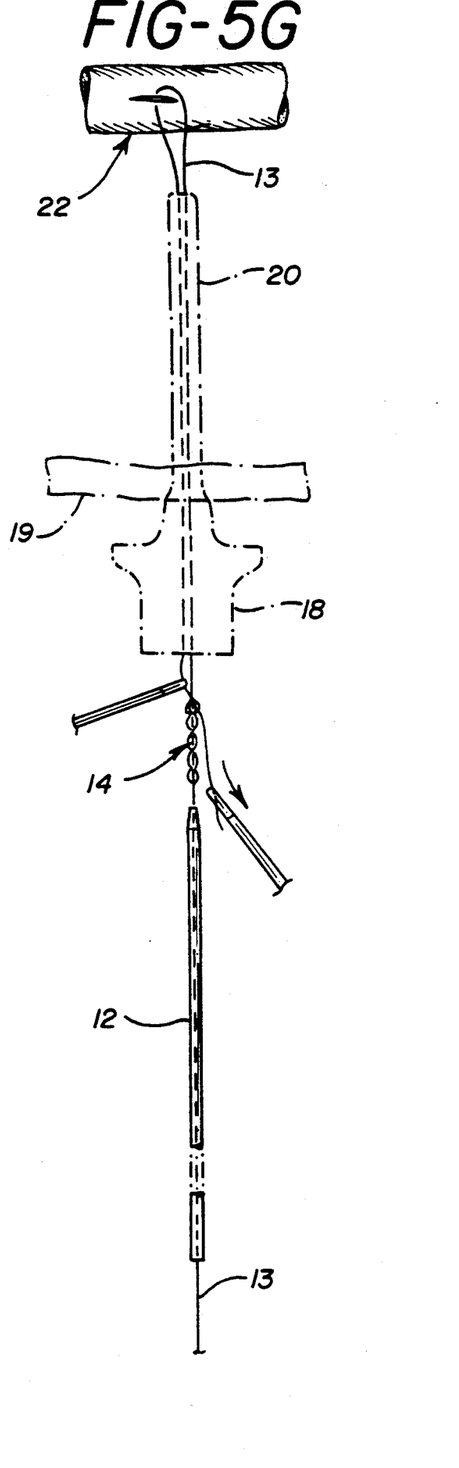
Figure 5H:
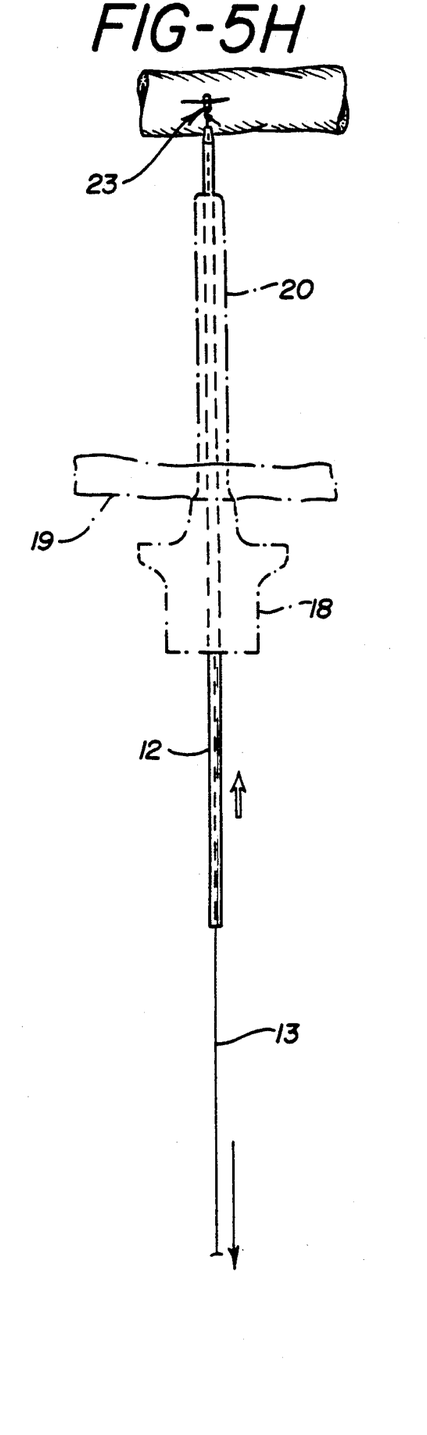

Once the user has a firm grip of that portion of the remaining strand protruding from the proximal end of the hollow tube, the user can then gently slide partially tightened slip knot 14 distally on the tube until it disengages from the tube and is engaged about the filamentary strand (FIG. 5F). As illustrated in FIG. 5G, the user of the device, while maintaining a firm grip on the portion of the filamentary strand protruding from the proximal end of the tube, can pull the pulling end 15 of the strand in the direction of the arrow as shown to fully tighten the knot. If desired, any excess suture strand on the pulling end can be removed. Once the knot is fully tightened, the user can then readily slide the knot distally on the filamentary strand by pushing the knot down with the tapered distal portion of the tube until it firmly engages tissue 22 (FIG. 5H). After the tissue approximation is completed, the user can then sever the filamentary strand at a location near the approximated tissue 22, and remove the tube from the trocar.

The method of using the device for ligation is substantially the same as the method described above for tissue approximation. The only significant difference is that the user would first remove the needle from the filamentary strand prior to inserting the distal end of the strand into and through the trocar. The needle is generally unnecessary for ligation because the strand can merely be looped around the vessel desired to be ligated. This looping procedure can be performed without penetrating tissue, so that the needle can be removed without affecting the ease with which the ligation can be performed.

Although this detailed description has focused on the preferred embodiment of the invention, it is readily apparent that numerous additional embodiments can be readily achieved without departing from the spirit and scope of the invention.

What is claimed is:

1. An improved endoscopic device of the type having a surgical needle; a hollow tube; and a filamentary strand attached at its distal end to the surgical needle, and slidable engaged at its proximal end about said tube with a partially tightened slip knot;

wherein the improvement comprises means for pulling the filamentary strand through the hollow tube proximally when the surgical needle is detached from the strand, wherein said means for pulling comprises:

a) a wire-like member extending through said hollow tube, said wire-like member attached at its proximal end to the proximal end of said hollow tube, and said wire-like member having a deformable distal loop thereon for receiving at least a portion of said filamentary strand, said deformable distal loop protruding from the distal end of said hollow tube; and b) a frangible proximal end portion on said hollow tube.

2. The device of claim 1 wherein said wire-like member is stainless steel wire.

3. The device of claim 2 wherein said deformable distal loop has a diameter greater than the inner cross-sectional diameter of said hollow tube.

4. The device of claim 3 wherein said deformable distal loop abuts the distal end of said hollow tube.

5. The device of claim 4 wherein said frangible proximal end portion is marked on said hollow tube with a score line.

6. The device of claim 5 wherein the partially tightened slip knot is engaged about the tube with five loops disposed around the circumference of the tube.

7. The device of claim 6 wherein the partially tightened slip knot terminates with a pulling end of the filamentary strand, wherein the slip knot can be fully tightened by pulling said pulling end.

8. The device of claim 7 wherein the slip knot, when fully tightened, allows sliding movement proximally and prevents sliding movement distally.

9. The device of claim 8 wherein the knot is tightened sufficiently to effectively ligate a bodily vessel or approximate tissue.

10. The device of claim 9 wherein the hollow tube has a tapered distal end.

11. The device of claim 10 wherein the hollow tube is composed of a flexible plastic.

12. The device of claim 11 wherein the filamentary strand is composed of a surgical suture material.

13. The device of claim 12 wherein the suture material is bioabsorbable.

* * * * *